(12) United States Patent
Macke

(10) Patent No.: US 10,751,186 B2
(45) Date of Patent: Aug. 25, 2020

(54) METHODS FOR ATTACHING ACETABULAR AUGMENTS TOGETHER OR TO ACETABULAR SHELLS

(71) Applicant: Zimmer, Inc., Warsaw, IN (US)

(72) Inventor: Jacob Macke, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 16/040,894

(22) Filed: Jul. 20, 2018

(65) Prior Publication Data

US 2019/0076256 A1 Mar. 14, 2019

Related U.S. Application Data

(60) Provisional application No. 62/557,382, filed on Sep. 12, 2017.

(51) Int. Cl.
*A61F 2/30* (2006.01)
*A61F 2/34* (2006.01)

(52) U.S. Cl.
CPC ...... *A61F 2/30734* (2013.01); *A61F 2/30771* (2013.01); *A61F 2/34* (2013.01); *A61F 2002/3069* (2013.01); *A61F 2002/3092* (2013.01); *A61F 2002/3093* (2013.01); *A61F 2002/3097* (2013.01); *A61F 2002/30131* (2013.01); *A61F 2002/30176* (2013.01); *A61F 2002/30181* (2013.01); *A61F 2002/30331* (2013.01); *A61F 2002/30387* (2013.01); *A61F 2002/30405* (2013.01); *A61F 2002/30428* (2013.01); *A61F 2002/30433* (2013.01); *A61F 2002/30448* (2013.01); *A61F 2002/30482* (2013.01); *A61F 2002/30507* (2013.01); *A61F 2002/30525* (2013.01); *A61F 2002/30553* (2013.01); *A61F 2002/30578* (2013.01);
(Continued)

(58) Field of Classification Search
CPC .... A61F 3/30749; A61F 2/30734; A61F 2/34; A61F 2002/3429; A61F 2002/343
See application file for complete search history.

(56) References Cited

U.S. PATENT DOCUMENTS 5,176,711 A * 1/1993 Grimes .............. A61B 17/1666
623/22.22
5,326,367 A * 7/1994 Robioneck ......... A61B 17/8066
623/22.35
(Continued)

FOREIGN PATENT DOCUMENTS

WO WO-2011156504 A2 12/2011

*Primary Examiner* — Alvin J Stewart
(74) *Attorney, Agent, or Firm* — Schwegman Lundberg & Woessner, P.A.

(57) ABSTRACT

Systems and methods and augments for supporting an acetabular shell at a hip bone. An example system of modular augments can include first and second augments, each having a body extending from a respective first end portion to a respective second end portion. The first augment second end portion can include a first coupling element and the second augment first end portion can include a second coupling element. Together the first and second coupling elements can form a coupling mechanism to join the first and second augments together. In some examples, the coupling mechanism can include a bulbous tip portion and a recess to receive and retain the bulbous tip portion.

20 Claims, 11 Drawing Sheets

(52) U.S. Cl.
CPC ............... *A61F 2002/30736* (2013.01); *A61F 2002/30784* (2013.01)

(56) References Cited

U.S. PATENT DOCUMENTS

| | | | | |
|---|---|---|---|---|
| 5,871,548 | A * | 2/1999 | Sanders | A61F 2/34 606/71 |
| 5,916,268 | A * | 6/1999 | Schollner | A61B 17/1746 623/22.36 |
| 6,162,257 | A * | 12/2000 | Gustilo | A61B 17/15 623/22.32 |
| 6,416,553 | B1 * | 7/2002 | White | A61B 17/1666 623/22.38 |
| 6,454,809 | B1 * | 9/2002 | Tornier | A61F 2/30724 623/22.32 |
| 7,291,177 | B2 * | 11/2007 | Gibbs | A61F 2/30724 623/22.25 |
| 7,476,254 | B2 * | 1/2009 | White | A61B 17/8066 623/22.32 |
| 7,597,715 | B2 * | 10/2009 | Brown | A61F 2/34 623/22.12 |
| 7,635,391 | B2 * | 12/2009 | Karrer | A61B 17/8066 623/23.14 |
| 7,993,408 | B2 | 8/2011 | Meridew et al. | |
| 8,021,432 | B2 * | 9/2011 | Meridew | A61F 2/30724 623/22.32 |
| 8,048,166 | B2 * | 11/2011 | Brown | A61F 2/30721 623/22.21 |
| 8,123,814 | B2 * | 2/2012 | Meridew | A61F 2/30734 623/22.19 |
| 8,663,333 | B2 * | 3/2014 | Metcalfe | A61F 2/4014 623/19.11 |
| 8,828,089 | B1 * | 9/2014 | Perez | A61F 2/30734 606/91 |
| 9,248,023 | B2 * | 2/2016 | Ries | A61F 2/30721 |
| 9,814,582 | B2 * | 11/2017 | Shea | A61F 2/30734 |
| 9,889,013 | B2 * | 2/2018 | Shea | A61F 2/30734 |
| 9,931,210 | B2 * | 4/2018 | Anderson | A61F 2/30734 |
| 2005/0021148 | A1 * | 1/2005 | Gibbs | A61F 2/30724 623/22.12 |
| 2005/0071014 | A1 * | 3/2005 | Barnett | A61F 2/28 623/19.14 |
| 2005/0187637 | A1 * | 8/2005 | Karrer | A61B 17/8066 623/22.24 |
| 2007/0250175 | A1 * | 10/2007 | Meridew | A61F 2/30724 623/22.21 |
| 2008/0021568 | A1 | 1/2008 | Tulkis et al. | |
| 2012/0016487 | A1 | 1/2012 | Conway et al. | |
| 2013/0035766 | A1 * | 2/2013 | Meridew | A61F 2/34 623/22.21 |
| 2014/0172113 | A1 * | 6/2014 | Shea | A61F 2/30734 623/22.21 |
| 2016/0317308 | A1 * | 11/2016 | Shea | A61F 2/30734 |
| 2017/0181856 | A1 * | 6/2017 | Anderson | A61F 2/30734 |
| 2018/0263781 | A1 * | 9/2018 | Anderson | A61F 2/30734 |
| 2019/0224014 | A1 * | 7/2019 | Guo | A61F 2/30734 |

* cited by examiner

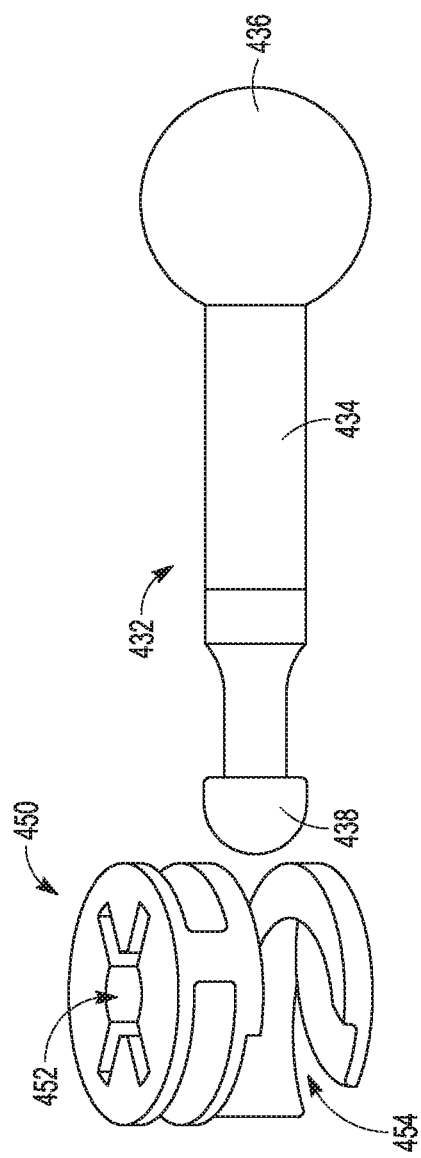

METHODS FOR ATTACHING ACETABULAR AUGMENTS TOGETHER OR TO ACETABULAR SHELLS

CLAIM OF PRIORITY

This application claims the benefit of U.S. Provisional Patent Application Ser. No. 62/557,382, filed on Sep. 12, 2017, the benefit of priority of which is claimed hereby, and which is incorporated by reference herein in its entirety.

TECHNICAL FIELD

This document pertains generally, but not by way of limitation, to orthopedic devices, and, more particularly, to augments that support acetabular implants used in total hip arthroplasty.

BACKGROUND

A total hip arthroplasty (THA) procedure can be performed to repair a diseased or damaged hip joint and replace it with a hip prosthesis. Sometimes, as with any other mechanical device, a total hip replacement can be subject to various forms of mechanical or biological issues. When issues occur, a reoperation of the hip prosthesis can be necessary to resolve the issues. Such a reoperation of a THA is called a revision THA. This is usually done several years after the original implantation and is more common in patients who had the initial THA performed at a young age and the patient chose to have a very active physical lifestyle.

One of the challenges of a THA, including a revision THA is how to securely implant the hip prosthesis. In particular, it can be challenging to securely implant an acetabular shell of the prosthesis into the remaining bone of the patient, especially in the presence of poor bone quality or bone loss.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 4A also shows an example attachment to the acetabular shell, in accordance with at least one example.

FIG. 4C is a side perspective view of an illustrative cam lock mechanism that can be used in the illustrative modular augments of FIGS. 4A and 4B, in accordance with at least one example.

DETAILED DESCRIPTION

Figure 1A:
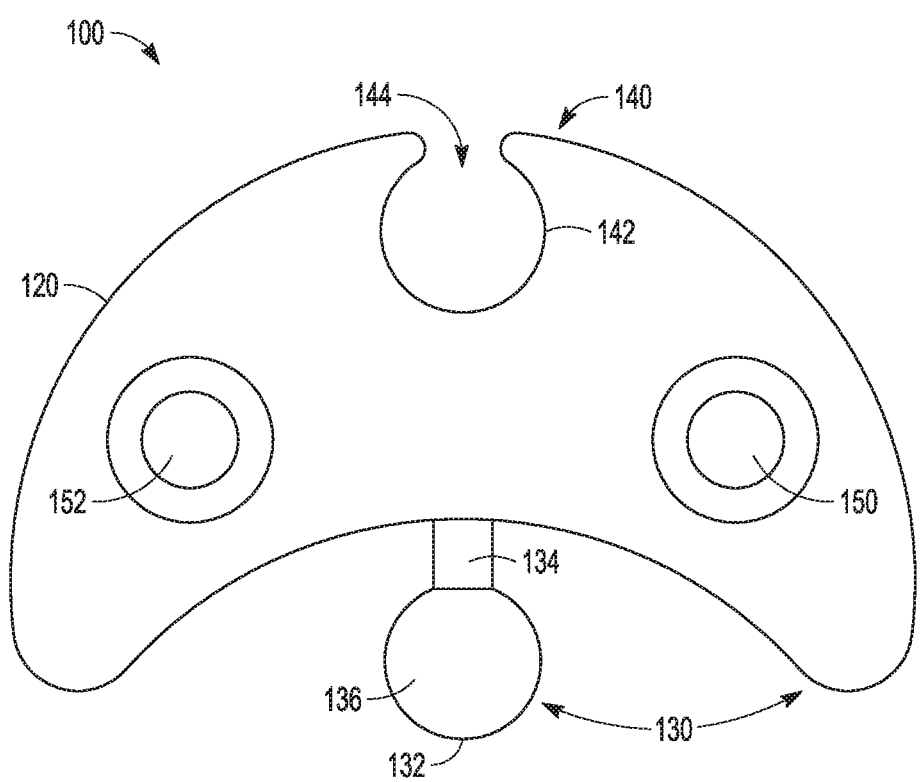
FIG. 1A is a top view of an illustrative modular augment, in accordance with at least one example.

As discussed above, one of the challenges of a total hip arthroplasty (THA), including a revision THA, is how to securely implant the hip prosthesis. In particular, it can be difficult to implant an acetabular revision shell of the prosthesis into the remaining bone of the patient, especially in the presence of poor bone quality or bone loss.

When using acetabular revision shells, surgeons can employ the use of additional augments to reinforce the attachment of the shell to the bone. Additional components can include a cup-cage construct. Cup-cage constructs can be used when the surgeon determines there is a risk of an acetabular cup migrating or loosening. The cage holds the acetabular cup (e.g., shell) in place long enough to provide biological fixation to the acetabular cup. However, the cup-cage construct reduces an allowable head size that can be placed in the acetabular cup.

In addition, surgeons are limited to "off the shelf" augment options, such as buttress and flange augments, having specified dimensions. These off the shelf augments limit the surgeon's ability to match the implant to the specific needs and dimensions of the patient. The surgeon, selecting from these off the shelf options, is limited in finding a best match for fixing the shell to the available bone. When the augments are too large or too small and the surgeon tries to match the augments up with the available bone, it does not always produce the desired results. Too small of an augment might not be able provide the desired fixation of the implant to the bone, while too large of an augment can interfere with the patient's anatomy adjacent the implant site.

The other option available to surgeons is to have a patient specific, fully customized implant manufactured. This option also has issues. Fully customized implants are not readily available off the shelf. They are manufactured to match a particular patient based on imaging data for the particular patient.

To address these issues, improved augments and methods for supporting acetabular shells are described herein. The augments and methods can include modular augments to increase the customizability in order to better match the anatomy of a patient. The modular augments have been found by the inventors to solve the problem of providing sufficient support in revision total hip arthroplasty (THA), while providing the ability to limit or extend the size of the augment to match the needs of the patient. The modular augments, systems and methods can allow tailored fixation of the augment to a particular patient. In other words, the improved augments can provide individualized customization to the particular patient's anatomy in an "off the shelf" design by using a modular approach. Some advantages of the improved augments can include: providing flexibility to the surgeon for selecting augment sizes that match the native bone, as well as preserving a maximized head size within the shell because the use of a cage of a cup-cage construct can be eliminated. In addition, the modular approach provides a system of modular augments that can be rotated relative to one another. This rotation features allows the resulting augment to better match the contour of the particular patient's hip bone.

The augments and methods disclosed herein can improve surgeon options for attaching acetabular shells to an acetabulum of patient in a more customizable manner, and without the expense of a fully customized, patient-specific implants. Because the modular augments are more customizable to the patient over conventional augments, the quality of the implantation can be made more reliable. The modular augments and methods in this disclosure can also be applied to non-revision, or first time THA surgeries and prosthesis.

For the sake of describing the system of modular augments, the modular augments will be described using terms such as first, second and third augments, however, a specific number and order of the modular augments is not necessarily required.

The modular augments can be described as being proximally or distally located to show relative placement in relation to the shell that the augments support. In some examples, the features in one modular augment can be present in another modular augment of the system, although all the features of one augment need not necessarily be present in the other modular augments. As described herein, the term "proximal" is generally associated with being proximate to or in a direction towards the acetabular shell, and the term "distal" is generally associated with being distal of or in a direction away from the shell.

Figure 1B:
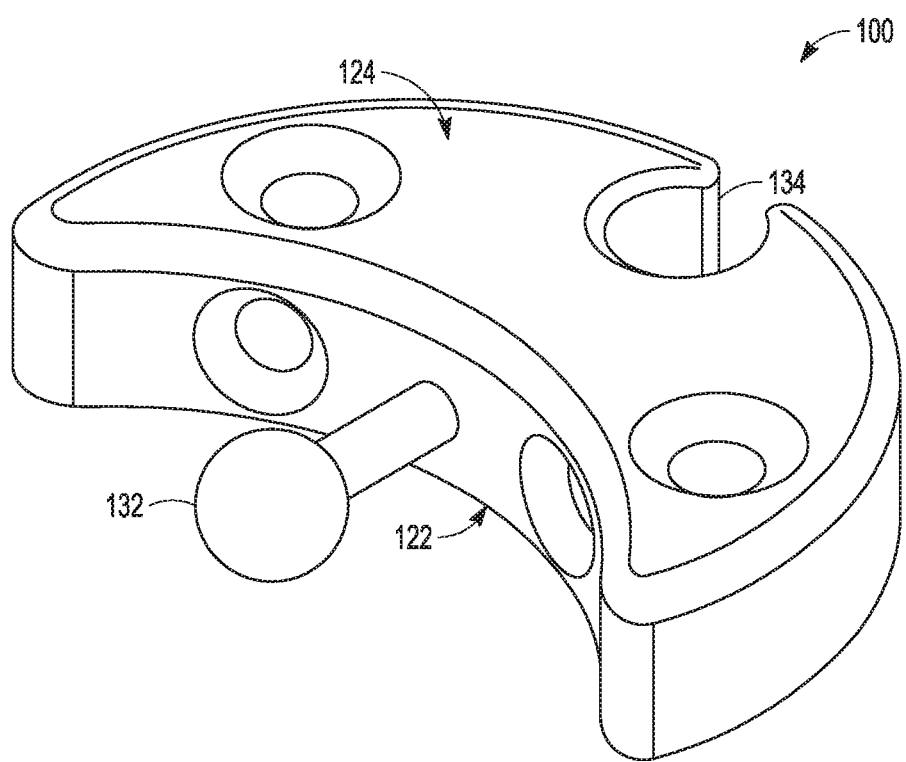
FIG. 1B is a perspective view of the illustrative modular augment of FIG. 1A, in accordance with at least one example.

FIGS. 1A and 1B show top and perspectives views of an illustrative modular augment 100 for supporting an acetabular shell at a bone, in accordance with at least one example.

Figure 2:
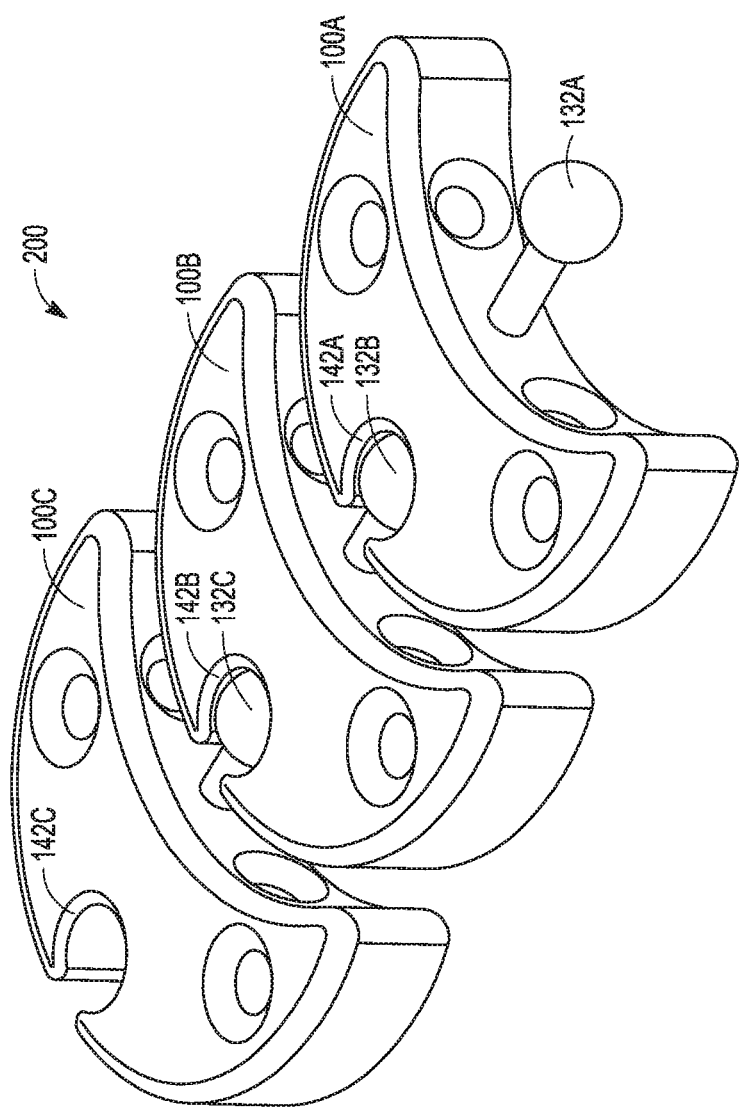
FIG. 2 is a perspective view of an illustrative system of three of modular augments shown coupled in a chain arrangement. Each of the three modular augments can be like the modular augment of FIG. 1A, in accordance with at least one example.

FIG. 2 shows the modular augment 100 of FIGS. 1A and 1B as part of a system 200 including a plurality of modular augments, hereinafter system 200. The plurality of modular augments (e.g., shown as three of modular augments 100) can include a first augment 100A, a second augment 100B and a third augment 100C. The plurality of modular augments (e.g., 100A, 100B, 100C) can be identical or similar to one another as shown, however, in some examples, the plurality of modular augments (e.g., 100A, 100B, 100C) can be different from one another, or can be tailored to a particular position in the system 200. In some examples, the modular augments 100A, 100B, 100C can form a buttress-type augment.

Figure 3:
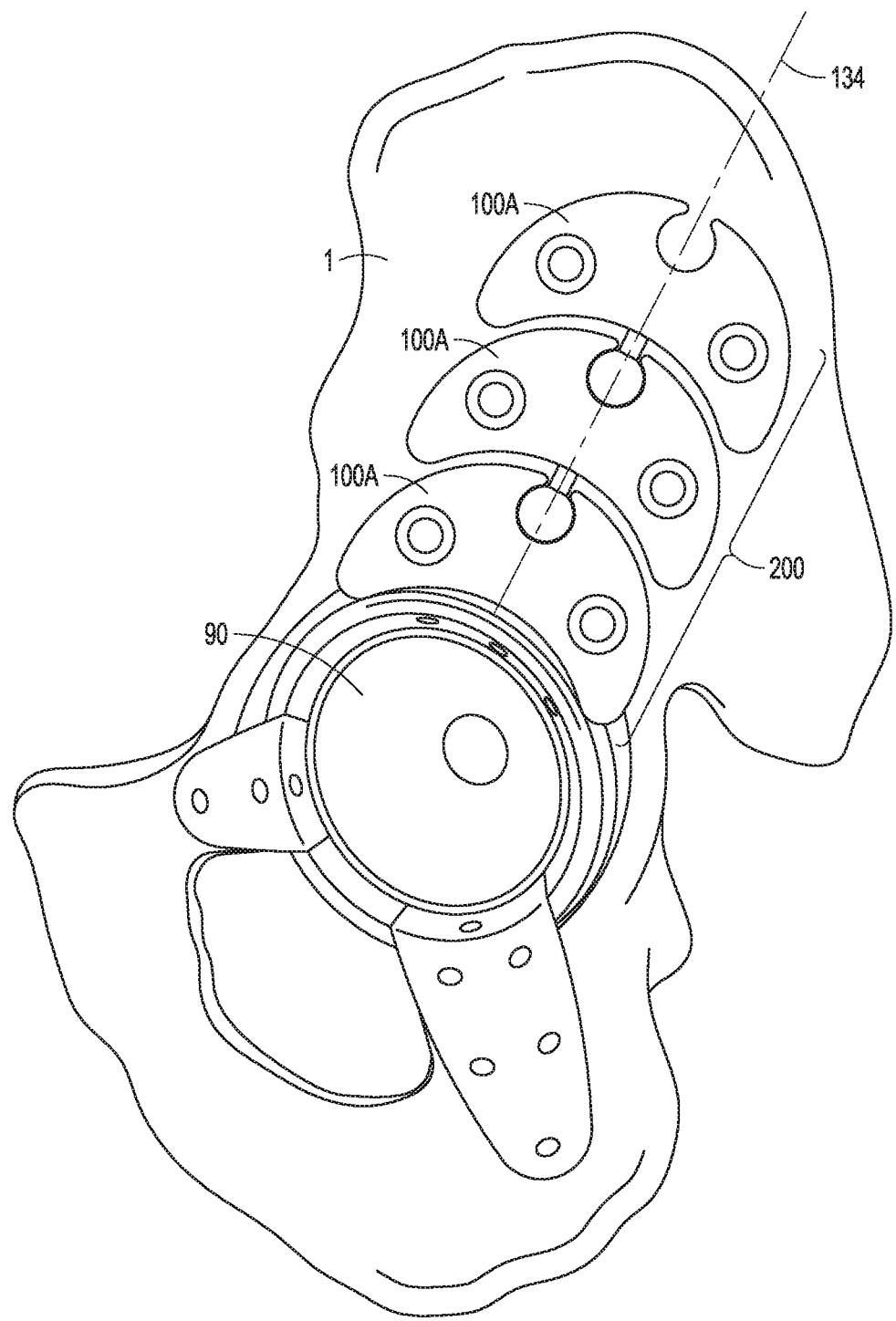
FIG. 3 is a top view of the illustrative modular augments of FIG. 2 positioned to support an acetabular shell at a hip bone, in accordance with at least one example.

FIG. 3 shows an example of the system 200 of FIG. 2 implanted at a hip bone 1 to support an acetabular shell 90. FIG. 3 will be described in further detail in this disclosure but is introduced here to show an example of the relative placement of the modular augments 100A, 100B, 100C at a hip when implanted at a hip bone 1. Note: in FIG. 3, a portion of the first augment 100A related to a coupling element to be described is not viewable, and/or may not be provided in some examples.

With reference to the modular augment 100 of FIGS. 1A and 1B, and with support from FIGS. 2 and 3, the modular augment 100 can include a body 120 having a first surface 122 (FIG. 1B) arranged to face a bone 1 (e.g., bone shown in FIG. 3), and a second surface 124 opposite the first surface 122 arranged to face away from the bone 1. To fasten the augment 100 to the bone 1, the augment 100 can include a first hole 150 and a second hole 152. Each of the first and second holes 150, 152 can extend through the body 120 of the augment 100 from the first surface 122 to the second surface 124. Screws or other fasteners can be inserted through the first and second holes 150, 152 to secure the augment 100 to the bone 1. In some examples, a combination of bone cement and fasteners can be used, or the augment can have a porous surface to contact the bone and allow bony ingrowth. In some examples, the first and second holes 150, 152 can be omitted and the augment 100 can be attached to the bone 1 with bone cement, or by any other suitable method.

The body 120 can extend from a first end portion 130 to a second end portion 140 (FIG. 1A). The modular augment 100 can be described as including, but is not limited to, an augment 100 having a generally crescent, lune or hemispherical shape. The augment 100 is not limited to these shapes, other shapes that can be nested together to support a shell 90, can be provided. Shapes including a U-shape, V-shape, Y-shape or irregular shaped body, or any other suitable shaped body for supporting a shell can be provided.

The modular augment 100 can be configured to be coupled to other similar or dissimilar modular augments. In the example modular augment 100, the first end portion 130 can include a first coupling element 132, and the second end portion 140 can include a second coupling element 142. When provided in a system with other augments (e.g., system 200, FIG. 2), the first coupling element 132 and the second coupling element 142 of two adjacently-located augments can be used to couple a plurality of the modular augments 100 of the system 200 together to form a single augment. A benefit of the modular augment system 200 is that it can be customized to fit a particular patient's anatomy, such as shown for modular augments 100A, 100B and 100C in FIGS. 2 and 3.

To facilitate coupling one a modular augment 100 (FIG. 1) to another modular augment 100 of the system 200 (e.g., 100A, 100B, 100C), the modular augment 100 will be described with reference to the second augment 100B of FIG. 2 for convenience because it is shown coupled in between two other augments in a chain-like arrangement. As shown in FIG. 2, the first coupling element 132B of the second augment 100B can be coupled to a second coupling element 142A of the (proximally-located) first augment 100A. Together, the first augment 100A second coupling element 142A and the second augment 100B first coupling element 132B can form a coupling mechanism. The coupling mechanism can join the first augment 100A and the second augment 100B of the system 200 together.

For example, as shown in FIG. 1, the first coupling element 132 can include the extension 134 having a bulbous tip portion 136, and the second coupling element 142 can include a recess 144 sized and shaped to receive either of both of the extension 134 and the bulbous tip portion 136.

In some examples of the first and second coupling elements 132, 142 can be placed in the opposite arrangement on the augment 100 with respect to the first end portion 130 and the second end portion 140 than is shown in FIG. 1A.

Regardless of the which end portion the first and second coupling elements 132, 142 are provided on, whether as shown in FIGS. 1A, 1B, 2 and 3, or the reverse arrangement, when incorporated into the system 200 of FIG. 2, the first and second coupling elements 132, 142 can form a coupling mechanism. In other words, the coupling mechanism can include either one of the first augment 100A second coupling element 142A or the second augment 100B first coupling element 132B having the extension (e.g., 134) and the bulbous tip portion (e.g., 136), while the other one of the first augment 100A second coupling element 142A or the second augment 100B first coupling element 132B can include the recess (e.g., 144) to receive the bulbous tip portion 136.

To extend the length of the system of modular augments 200 further, the second augment 100B second end portion 140B can include the second coupling element 142B for coupling to a distally-located third augment 100C. The system 200 can be extended to include as few or as many augments 100 as desired.

Although the modular augment 100 is described primarily with respect to the second augment 100B as the focus, with regard to the coupling mechanisms provided in all of the first, second and third augments 100A, 100B, 100C, the first coupling element 132A, 132B, 132C of any of the first, second or third augments 100A, 100B, 100C can include the extension 134A, 134B, 134C having the bulbous tip portion 136A, 136B, 136C, and the second coupling element 142A, 142B 142C of any of the modular augments 100A, 100B, 100C can include the recess 144A, 144B, 144C sized and shaped to receive the extension (e.g., 134) having the bulbous tip portion 136A, 136B, 136C. However, in other examples the arrangement of the bulbous tip portion 136A, 136B, 136C and the recess 144A, 144B, 144C in any of the modular augments 100A, 100B, 100C can be reversed as previously described.

FIG. 3 shows a top view of the modular augments 100A, 100B, 100C arranged around an acetabular shell 390 at a hip bone 1, in accordance with at least one example. Note that in FIG. 3, a portion of the first augment 100A is not viewable.

The first, second and third augments 100A, 100B, 100C can be positioned on the hip bone 1 in a chain-like arrangement extending away from the shell 90. In some examples, the modular augments 100A, 100B, 100C can be described as extending away from the shell 90 generally along an axis 134. The augments 100A, 100B, 100C can extend along the axis 134 in alignment with the axis 134, or can extend along the axis 134 without being aligned to the axis 134. The axis 134 can be a radially or non-radially extending axis. Likewise, any of the coupling elements 132A, 142A, 132B, 142B, 132C and 142C may also extend generally along such an axis 134, with or without being aligned to the axis 134.

Although the augments 100A, 100B and 100C can be engaged, nested and/or interlocked with one another by complementary body 120 (FIG. 1A) shapes and coupling mechanisms (e.g. 142A, 132B, FIG. 2) as described, the augments 100A, 100B and 100C can remain rotatable in three dimensions with respect to each other by the bulbous tip portion 136 (FIG. 1A). In some examples, the bulbous tip portion 136 can have a substantially spherical shape. A benefit of a spherical shape is that that it can rotate in three-dimensions in the recess 144 (FIG. 1) to adjust an orientation of one modular augment with respect to another modular augment. However, any suitable shape can be provided, including, but not limited to, a semi-spherical section, a wedge or a tear drop shaped bulbous tip portion 136.

To fix two of the modular augments together (e.g., 100A, 100B) and prevent rotation, the modular augments 100A, 100B can be cemented together at or adjacent any of the coupling mechanisms (e.g., 142A, 132B). For example, the first augment 100A can be fixed to the second augment 100B by applying bone cement over the coupling mechanism (142A, 132B).

As shown in FIG. 3, in order for the modular augments 100A, 100B, 100C to support the acetabular shell 90, the first end portion (e.g., 130, FIG. 1) of the first augment 100A can be adapted to be fixed to the acetabular shell 90 to support the shell 90. In some examples, and as shown here in FIG. 3, the first coupling element 132A (shown in FIG. 2) of the first augment 100A can be absent or can be removed by the surgeon. With the first coupling element 132A absent, the first augment 100A can be cemented to and/or screwed to the acetabular shell 90. In other examples, the first coupling element 132A (FIG. 2) of the first augment 100A can be coupled to the shell 90. One such example of a first augment 100A coupled to a shell 90 is shown and described with reference to FIGS. 4A and 4B (e.g., first augment 400A and shell 490A, 490B).

In some examples, and as previously described, the modular augment 100 can include a porous material that promotes boney ingrowth (e.g., supports boney ingrowth). In some examples, the modular augment 100 can be made partly or entirely of the porous material, partly or entirely of a solid material that is generally non-porous (e.g., solid metal, solid polymeric material), or a combination of both solid and porous materials. The augment 100 can also include smooth generally non-porous surfaces as well.

In the example shown in FIG. 1B, the second surface 124 can include a smooth, generally non-porous surface (e.g., most or all of the second surface 124 can be a smooth, non-porous surface) and can be adapted to face away from the bone surface when implanted. One benefit of the second surface 124 being smooth can be that it allows the second surface 124 not to irritate the tissues, including muscle tissue that is adjacent the modular augment 100 and covering the bone 1 (FIG. 3).

In contrast to the smooth, generally non-porous second surface 124, the first surface 122 can be adapted to mate with the bone 1 (FIG. 3) surface when implanted and can include the porous material that promotes boney ingrowth. One benefit of having the first surface 122 being porous material can be that it promotes boney ingrowth for better fixation to the bone 1. Boney ingrowth into the porous material can provide a stronger structural connection to the bone 1 as the bone 1 grows into the porous material over time.

Another benefit of the porous material at the first surface 122 can be that the porous surface exhibits a high coefficient of friction against the bone which can provide enhanced stability. In the example of FIG. 1B, the first surface 122 can have a first coefficient of friction, and the second surface 124 can have a second coefficient of friction. The first coefficient of friction can be less than the second coefficient of friction. This arrangement can improve the grip between the bone and the first surface 122 of the augment 100, while allowing the muscle tissue over the hip bone 1 to glide over the second surface 124 of the augment 100.

To facilitate boney ingrowth, any of the augments described herein can be formed of a three-dimensional structure that promotes (e.g., supports) boney ingrowth. For example, a highly porous, three-dimensional metallic structure can be provided that incorporates one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing boney tissue or other tissue to grow into the porous structure over time to enhance fixation (e.g., osseointegration) between the structure and surrounding bodily structures. According to certain examples of the present disclosure, an open porous metal structure, or a portion thereof, can have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal™ Technology available from Zimmer, Inc., of Warsaw, Ind. Trabecular Metal™ is a trademark of Zimmer, Inc. Such a material can be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure will be fabricated using a selective laser sintering (SLS) or other additive manufacturing-type process such as direct metal laser sintering or electron beam melting. In one example, a three-dimensional porous article is produced in layer-wise fashion from a laser-fusible powder, e.g., a single-component metal powder, which is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain examples, a laser selectively fuses powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In some examples, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate can be in direct contact with the ligaments of the highly porous structure, for example, approximately 15%, 20%, or 25%, of the surface area of the substrate can be in direct contact with the ligaments of the highly porous structure.

A highly porous, three-dimensional metallic structure can be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain examples, an open porous metal structure can be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure can have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

In some examples, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi™ is highly biocompatible, has high corrosion resistance and includes a highly interconnected porous architecture that mimics the porous structure of human cancellous bone, which can enhance bone integration and in-growth. In one exemplary implementation, OsseoTi™ can include a porous construct with a porosity.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Other examples of coupling mechanisms for joining a system of modular augments together are shown and described with reference to FIGS. 4A-4C, 5, 6A and 6B.

Figure 4A:
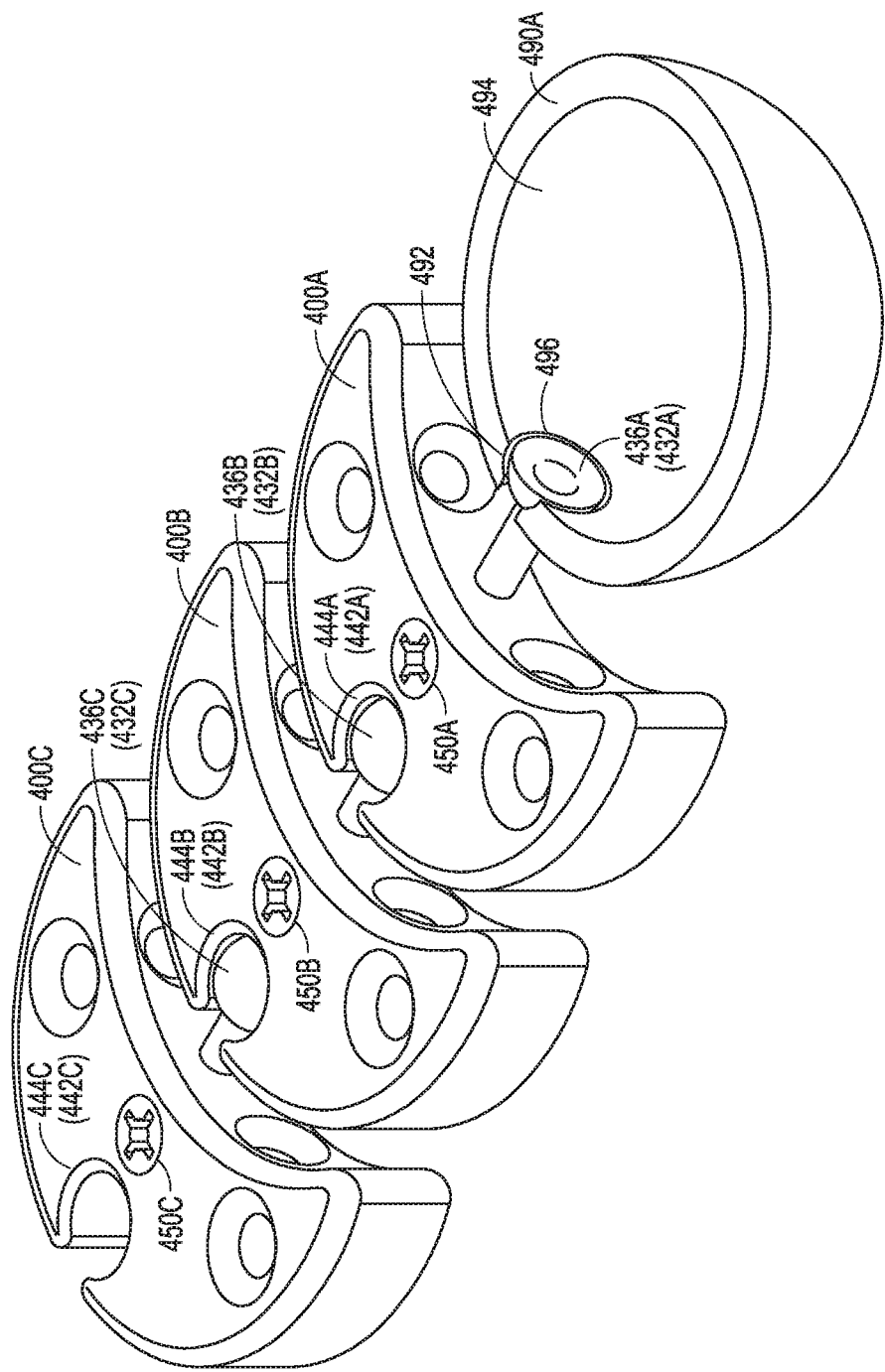
FIG. 4A is a perspective view of another example of three illustrative modular augments incorporating a cam lock mechanism. The modular augments are shown positioned to support an acetabular shell.
Figure 4B:
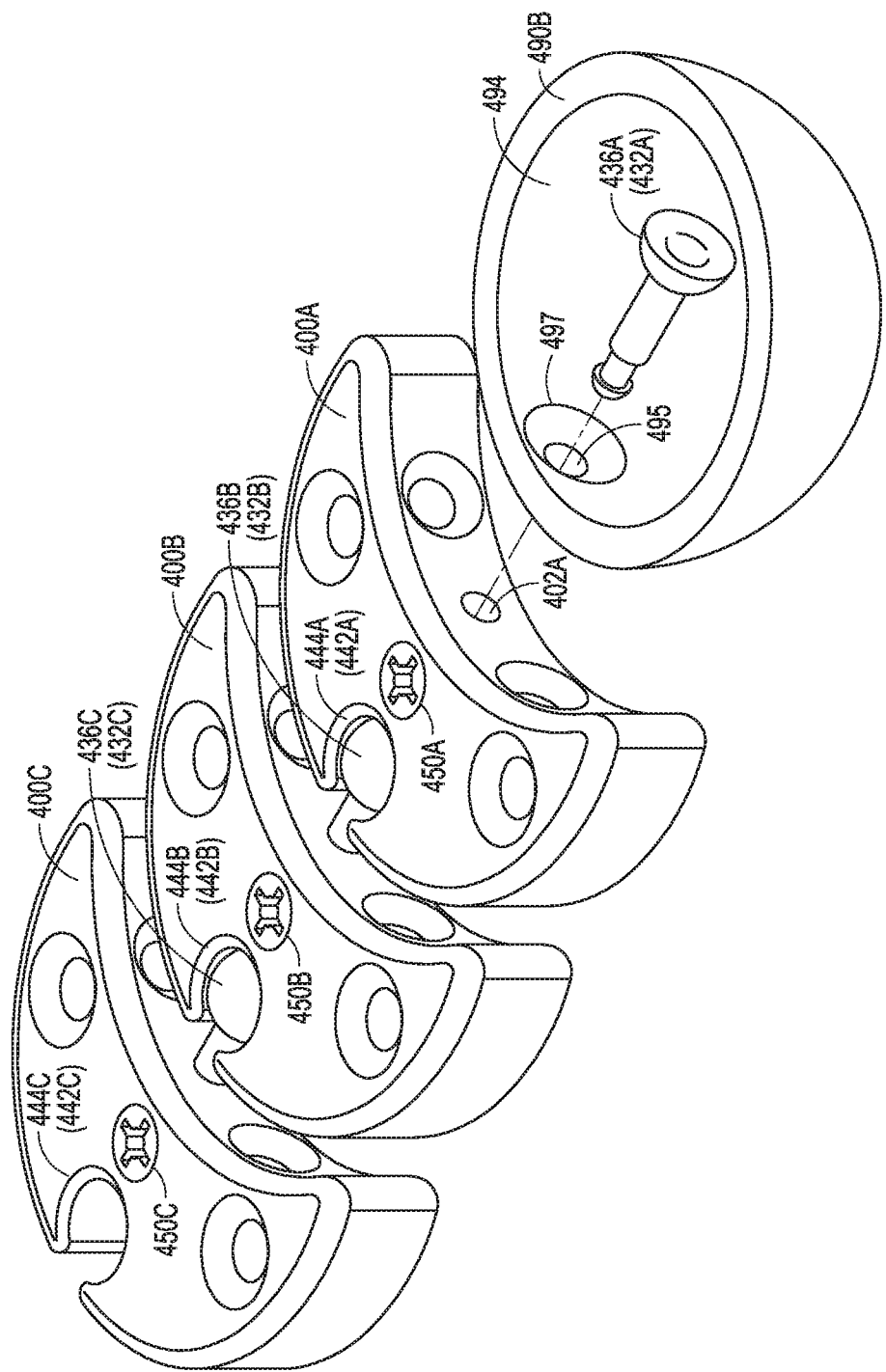
FIG. 4B includes the same system of modular augments as FIG. 4A showing another example of an attachment to the acetabular shell, in accordance with at least one example.

FIG. 4A shows a perspective view of another example of an illustrative system of modular augments incorporating a cam lock mechanism (FIG. 4C). The modular augments 400A, 400B, 400C are shown positioned to support an acetabular shell 490 in a manner similar to the system 200 of FIG. 2. FIG. 4A also shows an example attachment to the acetabular shell 490A, in accordance with at least one example. FIG. 4B shows the same modular augments 400A 400B, 400C as shown in FIG. 4A but show another example of an attachment to the acetabular shell 490B.

To facilitate coupling one of the modular augments 400A, 400B, 400C to another one of the modular augments 400A, 400B, 400C, the coupling arrangement will be described with reference to the second augment 400B for clarity because it is shown coupled in between two other augments 400A, 400C. Similar to the system 200 of FIG. 2, in FIGS. 4A and 4B, a first coupling element 432B of the second augment 400B can be coupled to a second coupling element 442A of the proximally-located first augment 400A. Together, the first augment 400A second coupling element 442A and the second augment 400B first coupling element 432B can form a coupling mechanism. The coupling mechanism can join the first augment 400A and the second augment 400B together in a chain like arrangement.

However, the coupling mechanism of FIGS. 4A and 4B can further include additional components in the coupling mechanism to secure the modular augments 400A, 400B, 400C together, instead of, or in addition to, using bone cement. As shown in FIGS. 4A and 4B, the coupling mechanism can incorporate a cam lock (e.g., at 450A, 450B, 450C) to provide additional security and to pull the augments 400A, 400B, 400C together. An example of a cam lock mechanism 450, 432 is shown in FIG. 4C. A cam lock mechanism 450, 432 is a fastening mechanism that incorporates a cam 450 that can be turned to engage a catch 438.

FIG. 4C shows a side perspective view of an illustrative cam lock mechanism 432, 450 that can be used in the illustrative modular augments 400A, 400B, 400C of FIGS. 4A and 4B. Turning cam 450 at head 452 of the cam 450 causes a catch 438 on the first coupling element 432 (located at an end of the first coupling element opposite a bulbous tip portion 436) to be locked into a variable-width groove 454 of the cam 450. Rotating the cam 450 causes the first coupling element 432 to be pulled inward (e.g. the first coupling element 432B can be translated inward with respect to the second augment 400B), thereby causing the bulbous tip portion 436B of the second augment 400B, to move closer to the second augment 400B. As the bulbous tip portion 436B translates inward towards the second augment 400B, it exerts a force on the recess 444A of the first augment 400A. A tension force can also be induced in the extension 434. This movement causes the first augment 400A and the second augment 400B to be pulled closer to one another and causes the bulbous tip portion 436B to be retained in the recess 444A. This example of a cam lock mechanism 432, 450 depicted in FIG. 4C can be provided in one or more of the augments 440A, 440B, 440C. For example, each of the first second and third augments 400A, 400B, 400C can include cam locks 450A, 450B, 450C, and corresponding first coupling elements of each of the modular augments 400A, 400B, 400C can include a catch (e.g., 438, FIG. 4C).

Also shown in FIGS. 4A and 4B, the first end portion (e.g., 430, FIG. 4B) of at least the first augment 400A can be adapted to be fixed to an acetabular shell 490, hereinafter shell.

For example, as shown in FIG. 4A, a first coupling element 432A of the first augment 400A can be coupled to an acetabular shell 490A (e.g., instead of being coupled to another modular augment). In FIG. 4A, the first augment 400A can include a first coupling element (e.g., including 432) that can be coupled with shell 490A to secure the first augment 400A to the shell 490A. As shown in FIG. 4A, the bulbous tip portion 436A of the first coupling element 432A can be inserted into a cutout 496 in the shell 490A. In some examples, the inside surface 494 of the shell 490, the cutout 496 can include a surface area shaped so that the bulbous tip portion 436A can lie flush or nearly flush with the inside surface 494 of the shell 490 such that a liner can be inserted without the bulbous tip portion 436A interfering with the insertion of the liner.

FIG. 4B can be identical to FIG. 4A, except for the attachment of the first augment 400A to the shell 490B. In FIG. 4B, the first coupling element 432A can be inserted through a hole 495 having a surrounding depression 497 in the shell 490B and into a cam access hole 402A in the augment 400A. Like the other cam lock mechanisms described with reference to FIG. 4A, when the cam 450A is turned, the cam lock mechanism secures the first augment 400A to the acetabular shell 490B.

Figure 5:
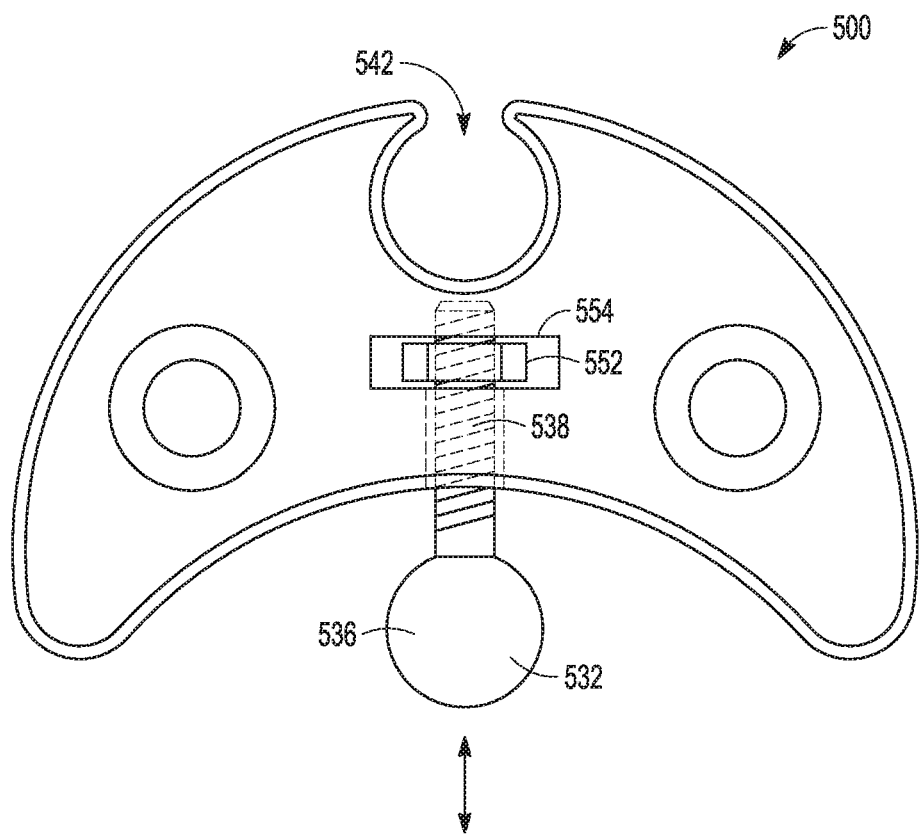
FIG. 5 is a top view of another illustrative modular augment including a captured nut, in accordance with at least one example.

FIG. 5 shows a top view of another illustrative modular augment 500 including a first coupling element 532 and a second coupling element 542. The modular augment 500 can include a captured nut, in accordance with at least one example. The modular augment of FIG. 5 can be used in system of modular augments and can be similar to other modular augments 100, 100A, 100B, 100C, 400A, 400B and 400C. While the previous modular augments 100, 100A, 100B, 100C, 400A, 400B, 400C describe securing two adjacent augments together with bone cement or a cam lock, FIG. 5 shows an example of a coupling mechanism including a captured nut 552 that can be accessed via a slot 554 in the augment 500. Like the cam lock of FIG. 4C, the captured nut 552 can cause the bulbous tip portion 536 to be pulled inward. The user can insert a tool into slot 554 and turn the nut 552. Turning the nut 552 can cause threads 538 on the first coupling element 532 to travel relative to the threads in the nut and pull the bulbous tip portion 536 inward. Consequently, turning the nut 552 in the other direction can move the bulbous tip portion 536 outward of the augment 500. The direction the bulbous tip portion 536 moves can be dependent on the direction the nut 552 is turned. FIG. 5 shows merely one illustrative example, in various examples, at least one of the first or second coupling elements 532, 542 can include the nut 552.

Figure 6A:
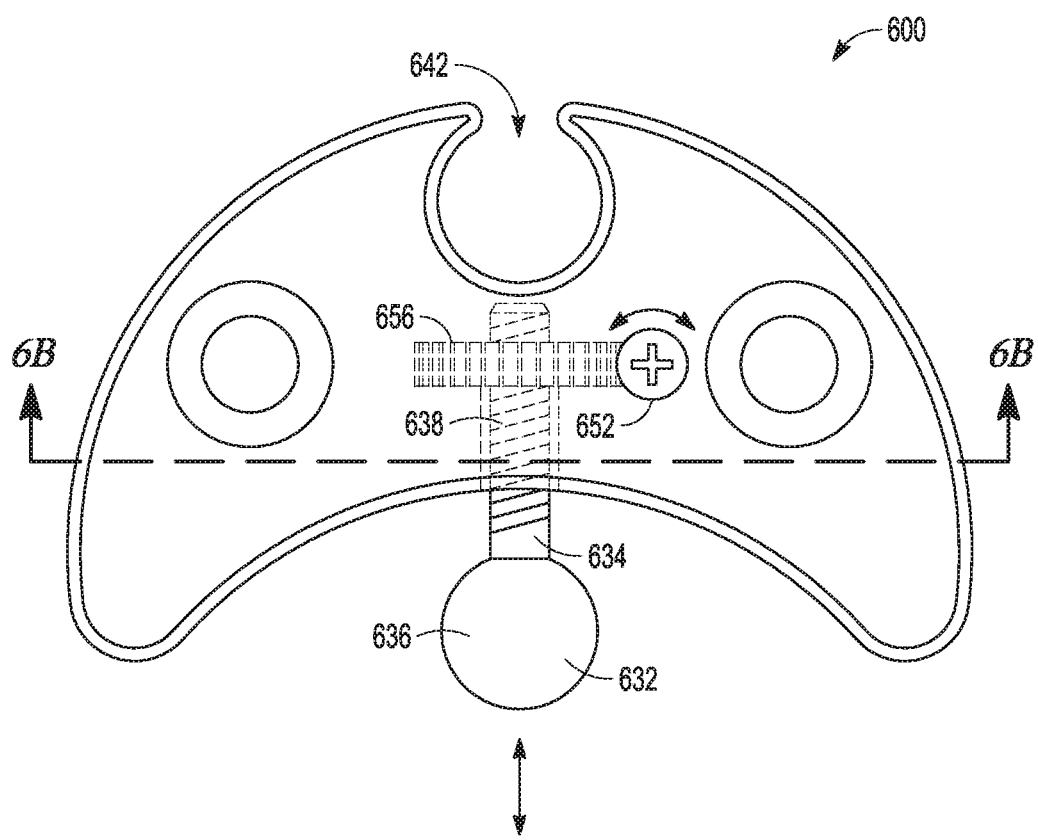
FIG. 6A is a top view of another illustrative modular augment including a gear mechanism, in accordance with at least one example.

FIG. 6A shows a top view of another illustrative modular augment 600 having a first coupling element 632 and a second coupling element 642. The modular augment 600 can include a worm drive mechanism 652, 654, 656, in accordance with at least one example. The worm drive 652, 654, 656, can, like the cam lock of FIGS. 4A-4C and the captured nut of FIG. 5, cause the bulbous tip portion 636 of the first coupling element 632 to be pulled inward of the augment 600. To better understand how the worm drive mechanism 652, 654, 656 can be operated, FIG. 6B is also provided and shows a cross-sectional side view of the illustrative augment of FIG. 6A along line A-A', in accordance with at least one example.

Figure 6B:
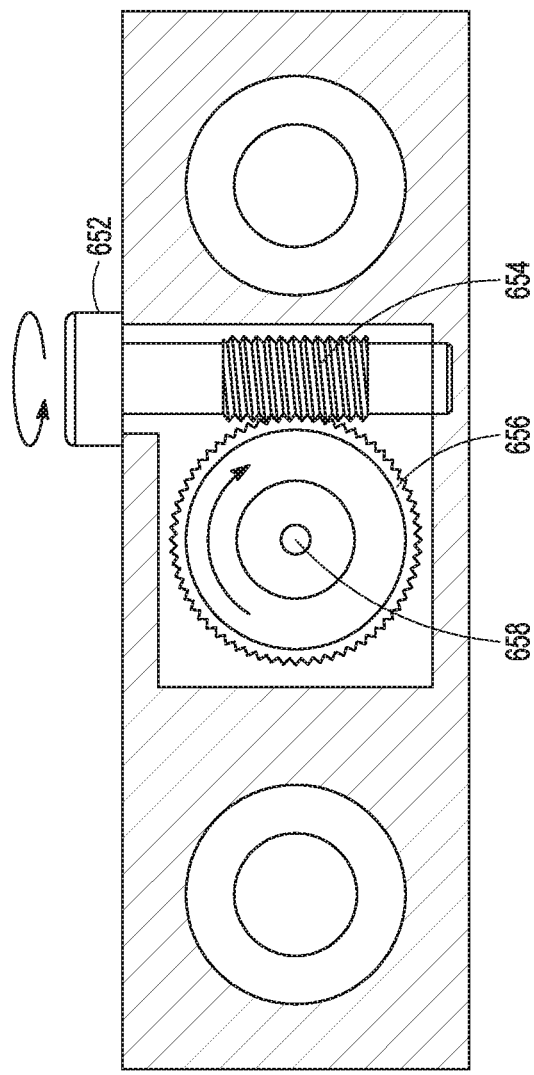
FIG. 6B is a cross-sectional side view of the illustrative modular augment of FIG. 6A along line A-A' in FIG. 6A, in accordance with at least one example.

As shown in FIGS. 6A and 6B together, to pull the bulbous tip portion 636 inward, the user turns a head 652 of a worm gear 646. As the user turns the head 652 (e.g., with a screw driver) the motion can be transferred from the worm gear 646 to worm wheel 656. Threads on an inside diameter 658 (FIG. 6B) of the worm wheel 656 cause the threads 638 on an extension 634 (FIG. 6A) of the first coupling element 632 to be pulled inward or outward, depending on the direction that the se 652 is turned. FIGS. 6A and 6B are provided merely as an illustrative example, in various examples, at least one of the first or second coupling elements 632, 642 can include the worm gear 646 and worm wheel 656.

Reasons the surgeon would use modular augments can include: the surgeon wants the flexibility to implant a smaller or larger augment than can be available in conventional augments. Increasing or decreasing the size of the augment to only what is needed in the particular patient provides the surgeon the ability to optimize the fit of the augment to the host bone. In addition to the fit being optimized, the need to remove additional host bone in order to achieve a natural implant positioning and orientation can be reduced. Achieving proper positioning of the shell can lead to improved hip kinematics in the patient.

The system of modular augments 200 can be particularly useful when there is lost or missing bone, as can be the case when a patient has Paprosky type IIIA defects. However, the illustrative modular augments 100A, 100B, 100C can also be used to address other issues and defects, and the features described herein can be used with other augments that are not related to addressing Paprosky rated defects.

Figure 7:
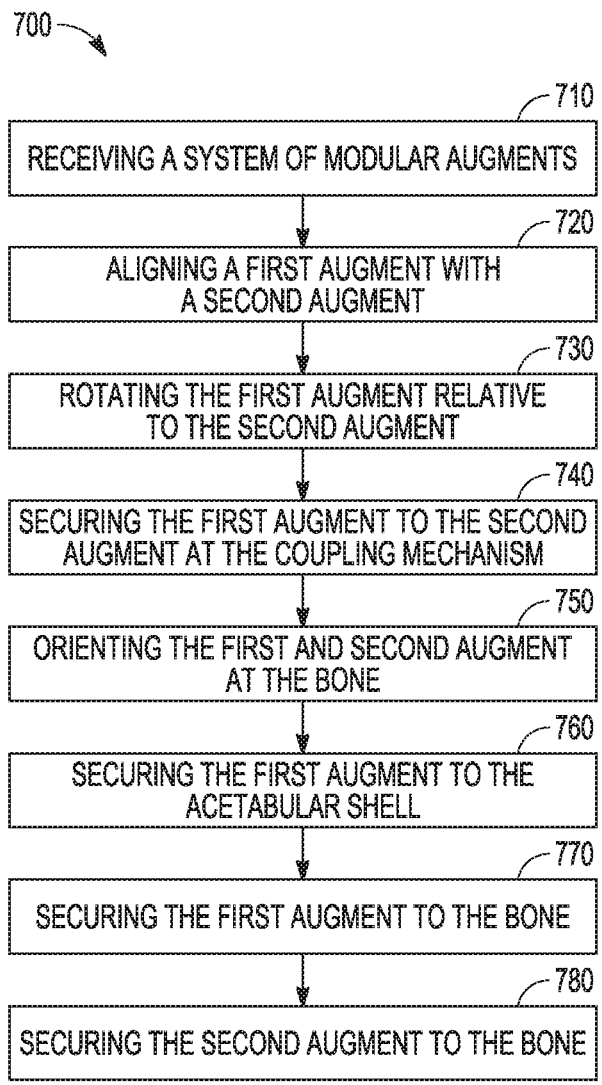
FIG. 7 is a flow chart illustrating a method of using modular augments to secure an acetabular shell to a bone of a patient, in accordance with at least one illustrative example.

FIG. 7 shows a flow chart illustrating a method 700 of using modular augments to secure an acetabular shell to a bone of a patient, in accordance with at least one illustrative example. The method 700 can be used with modular augments such as the modular augments of FIGS. 1A, 1B, 2, 3, 4A, 4B, 5 and 6, but can be used with other modular augments.

Step 310 can include receiving a system of modular augments as previously shown and described in FIGS. 1A, 1B, 2, 3, 4A, 4B, 5 and 6. The system can include a first augment and a second augment. Each of the first and second augments has a body extending from a first end portion to a second end portion. The first augment first end portion can include a first coupling element, and the first augment second end portion can include a second coupling element. The second augment first end portion can include a first coupling element. The first augment second coupling element and the second augment first coupling element can form a coupling mechanism.

Step 320 can include aligning the first augment second coupling element with the second augment first coupling element.

Step 330 can include rotating, for example, in three-dimensions, the first augment relative to the second augment to an orientation that complements a surface of a bone.

Step 340 can include securing the first augment to the second augment with the coupling mechanism. The coupling mechanism can include, for example, any of the coupling mechanism including a bulbous tip portion and a recess, or any other suitable coupling mechanism, including, but not limited to: a cam lock, a nut, or a gear. The securing the first augment to the second augment can include rotating a portion of a coupling mechanism. Including, but not limited to, rotating a cam lock or rotating a worm gear or other type of gear. The securing the first augment to the second augment can also include using bone cement.

Step 350 can include orienting the first and second augments at the bone. Examples of locations where the augments can be oriented on the bone can include: a superior position on an ilium of the bone, or an inferior position on an ischium or ramus of the bone. Any other suitable location for an augment can also be used.

Step 360 can include securing the first augment to the acetabular shell or to a proximally-located third augment.

Step 370 can include securing the first augment to the bone, for example by using screws and/or bone cement.

Step 380 can include securing the second augment to the bone at a location distal of the first augment. The second augment can be secured to the bone, for example, by using screws and/or bone cement.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

VARIOUS NOTES AND EXAMPLES

To better illustrate the devices and methods disclosed herein, a non-limiting list of embodiments is provided herein.

Example 1 is a system of modular augments for supporting an acetabular shell at a hip bone, the system comprising: a first augment; and a second augment, wherein each of the first and second augments has a body extending from a first end portion to a second end portion, wherein the first augment first end portion has a first coupling element, wherein the first augment second end portion has a second coupling element, wherein the second augment first end portion has a first coupling element, wherein the first augment second coupling element and the second augment first coupling element form a coupling mechanism to join the first augment and the second augment of the system of modular augments together, wherein one of the first augment second coupling element and second augment first coupling element comprises an extension having a bulbous tip portion and the other one of the first augment second coupling element and the second augment first coupling element comprises a recess to receive and retain the bulbous tip portion.

In Example 2, the subject matter of Example 1 includes, wherein the bulbous tip portion is three-dimensionally rotatable within the recess to adjust an orientation of the first augment with respect to the second augment.

In Example 3, the subject matter of Examples 1-2 includes, wherein the bulbous tip portion is substantially spherical.

In Example 4, the subject matter of Examples 1-3 includes, wherein the bulbous tip portion is substantially semi-spherical.

In Example 5, the subject matter of Examples 1-4 includes, wherein the coupling mechanism includes a cam lock.

In Example 6, the subject matter of Examples 1-5 includes, wherein the coupling mechanism includes a gear.

In Example 7, the subject matter of Examples 1-6 includes, wherein the coupling mechanism includes a worm gear.

In Example 8, the subject matter of Examples 1-7 includes, wherein the coupling mechanism includes a captured nut.

In Example 9, the subject matter of Examples 1-8 includes, wherein the coupling mechanism further comprises a rotatable nut or gear that when rotated translates the bulbous tip portion relative to the rotatable nut or gear.

In Example 10, the subject matter of Examples 1-9 includes, wherein the first augment second coupling element and the second augment first coupling element are shaped to interlock with one another.

In Example 11, the subject matter of Examples 1-10 includes, wherein the second augment second end portion has a second coupling element adapted to attach to a distally-located third augment.

In Example 12, the subject matter of Examples 1-11 includes, wherein the first end portion of the second augment is shaped to nest with the second end portion of the first augment.

In Example 13, the subject matter of Examples 1-12 includes, wherein when the first and second augments are coupled together and secured to the acetabular shell, the first and second augments form a single augment that extends in a direction away from the acetabular shell.

In Example 14, the subject matter of Examples 1-13 includes, wherein the first coupling element of the first augment first end portion is adapted to be coupled to a proximally-located third augment or an acetabular shell.

In Example 15, the subject matter of Examples 1-14 includes, wherein the first augment first coupling element is adapted to attach to a third augment, the third augment extending from a first end portion having a first coupling element to a second end portion having a second coupling element, wherein the third augment second coupling element has a complementary geometry to mate with the first augment first coupling element.

Example 16 is a method for securing an acetabular shell to a bone of a patient using a system of modular augments, the method comprising: receiving a system of modular augments including: a first augment and a second augment, wherein each of the first and second augments has a body extending from a first end portion to a second end portion, wherein the first augment first end portion has a first coupling element, wherein the first augment second end portion has a second coupling element, wherein the second augment first end portion has a first coupling element, wherein the first augment second coupling element and the second augment first coupling element form a coupling mechanism; aligning the first augment second coupling element with the second augment first coupling element; rotating in three-dimensions, the first augment relative to the second augment to an arrangement that complements a surface of the bone; securing the first augment to the second augment with the coupling mechanism; orienting the first and second augments at the bone; securing the first augment to the acetabular shell or to a proximally-located third augment; securing the first augment to the bone; and securing the second augment to the bone at a location distal of the first augment.

In Example 17, the subject matter of Example 16 includes, wherein securing the first augment to the second augment includes inserting an extension having a bulbous tip portion into a recess having a shape and a size to receive the bulbous tip portion, and inducing a tension force in the extension along a direction extending away from the bulbous tip portion.

In Example 18, the subject matter of Example 17 includes, wherein rotating in three-dimensions, the first augment relative to the second augment includes rotating the bulbous tip portion in the recess.

In Example 19, the subject matter of Examples 17-18 includes, wherein securing the first augment to the second augment includes rotating a rotation element of the first or second coupling element to translate the bulbous tip portion closer to the rotation element.

In Example 20, the subject matter of Examples 16-19 includes, wherein securing the first augment to the second augment includes adjusting the coupling mechanism formed by the first augment second coupling element and the second augment first coupling element to move the first and second augments closer together.

In Example 21, the subject matter of Examples 16-20 includes, wherein securing the first augment to the second augment includes rotating a cam lock of the coupling mechanism.

In Example 22, the subject matter of Examples 16-21 includes, wherein securing the first augment to the second augment includes rotating a gear of the coupling mechanism.

In Example 23, the subject matter of Examples 16-22 includes, wherein securing the first augment to the second augment includes rotating a worm gear of the coupling mechanism.

In Example 24, the subject matter of Examples 16-23 includes, applying bone cement over the coupling mechanism.

In Example 25, the subject matter of Examples 16-24 includes, times longer than a length of the first or a length of the second augment in the direction extending radially away from the acetabular shell.

In Example 26, the subject matter of Examples 16-25 includes, wherein the first and second augments are buttress augments.

In Example 27, the subject matter of Examples 16-26 includes, wherein orienting the first and second augments at the bone includes orienting the first and second augments at a superior position on an ilium of the bone.

In Example 28, the subject matter of Examples 16-27 includes, wherein orienting the first and second augments at the bone includes orienting the first and second augments at an inferior position on an ischium or ramus of the bone.

Example 29 is a modular augment of a system of modular augments for supporting an acetabular shell at a bone, the modular augment comprising: a body having a first surface arranged to face a bone, and a second surface opposite the first surface arranged to face away from the bone, the body extending from a first end portion to a second end portion, the first end portion having a first coupling element, and the second end portion having a second coupling element that is adapted to interlock with a distal coupling element of a distal modular augment.

In Example 30, the subject matter of Example 29 includes, wherein the first or second coupling element includes an extension having a bulbous tip portion.

In Example 31, the subject matter of Examples 29-30 includes, wherein at least one of the first or second coupling elements comprises a portion of a cam lock mechanism.

In Example 32, the subject matter of Examples 29-31 includes, wherein at least one of the first or second coupling elements comprises a gear.

In Example 33, the subject matter of Examples 29-32 includes, wherein at least one of the first or second coupling elements comprises a worm gear.

In Example 34, the subject matter of Examples 29-33 includes, wherein at least one of the first or second coupling elements comprises a captured nut.

In Example 35, the subject matter of Examples 29-34 includes, wherein at least one of the first or second coupling elements comprises a nut, that when rotated, causes the first or second coupling element to move relative to the modular augment.

In Example 36, the subject matter of Examples 29-35 includes, wherein at least one of the first or second coupling elements includes a recess sized and shaped to receive an extension having a bulbous tip portion.

In Example 37, the subject matter of Example 36 includes, wherein the recess is sized and shaped to retain the bulbous tip portion when a tension force is applied to the extension in a direction extending away from the bulbous tip portion.

In Example 38, the subject matter of Examples 29-37 includes, wherein the modular augment is a modular buttress augment.

In Example 39, the subject matter of Examples 29-38 includes, wherein the first end portion has a curved surface that is shaped to conform to a generally spherical surface portion of the acetabular shell.

In Example 40, the subject matter of Examples 29-39 includes, wherein the first coupling element is adapted to be coupled to a proximally-located modular augment.

In Example 41, the subject matter of Examples 29-40 includes, wherein the first coupling element is adapted to be coupled to an acetabular shell.

In Example 42, the subject matter of Examples 29-41 includes, wherein a perimeter of the body is generally crescent-shaped.

In Example 43, the subject matter of Examples 29-42 includes, wherein the first and second coupling elements extend along an axis from the first coupling element to the second coupling element.

In Example 44, the subject matter of Examples 29-43 includes, wherein the body comprises a porous material that promotes boney ingrowth.

In Example 45, the subject matter of Examples 29-44 includes, wherein the first surface comprises a porous material that promotes boney ingrowth adapted to face the bone when implanted, and wherein the second surface comprises a smooth surface adapted to face away from the bone when implanted.

In Example 46, the subject matter of Examples 29-45 includes, wherein the body is adapted to structurally support the acetabular shell in a patient having a Paprosky type IIIA defect.

Example 47 is an augment and acetabular shell system comprising: an acetabular shell having a first surface and a second surface, and an opening extending from the first surface to the second surface; an augment having a first coupling element; and an elongate coupling member having an extension portion and a bulbous tip portion, wherein the extension portion is adapted to extend through the opening from the first surface to the second surface, and the bulbous tip portion is adapted to be captured in the acetabular shell, wherein the first coupling element includes, a rotation element that when rotated, translates the elongate coupling member relative to the rotation element.

In Example 48, the subject matter of Example 47 includes, wherein the rotation element includes a cam lock.

In Example 49, the subject matter of Examples 47-48 includes, wherein the rotation element includes a gear.

In Example 50, the subject matter of Examples 47-49 includes, wherein the rotation element includes a worm gear.

In Example 51, the subject matter of Examples 47-50 includes, wherein the rotation element includes a captured nut.

In Example 52, the subject matter of Examples 47-51 includes, wherein the bulbous tip portion comprises a substantially semi-spherical shape.

Example 53 is at least one machine-readable medium including instructions that, when executed by processing circuitry, cause the processing circuitry to perform operations to implement of any of Examples 1-52.

Example 54 is an apparatus comprising means to implement of any of Examples 1-52.

Example 55 is a system to implement of any of Examples 1-52.

Example 56 is a method to implement of any of Examples 1-52.

What is claimed is:

1. A system of modular augments for supporting an acetabular shell at a hip bone, the system comprising:
   a first augment; and
   a second augment,
   wherein each of the first and second augments has a body extending from a first end portion to a second end portion,
   wherein the first augment first end portion has a first coupling element,
   wherein the first augment second end portion has a second coupling element,
   wherein the second augment first end portion has a first coupling element,
   wherein the first augment second coupling element and the second augment first coupling element form a coupling mechanism to join the first augment and the second augment of the system of modular augments together, wherein one of the first augment second coupling element and second augment first coupling element comprises an extension having a bulbous tip portion and the other one of the first augment second coupling element and the second augment first coupling element comprises a recess to receive and retain the bulbous tip portion, wherein the first end portion of the second augment is shaped to nest with the second end portion of the first augment when the bulbous tip portion is received within the recess, and wherein the coupling mechanism includes a rotation element that when rotated translates the bulbous tip portion relative to the rotation element.

2. The system of modular augments of claim 1, wherein the bulbous tip portion is three-dimensionally rotatable within the recess to adjust an orientation of the first augment with respect to the second augment.

3. The system of modular augments of claim 1, wherein the bulbous tip portion is substantially spherical.

4. The system of modular augments of claim 1, wherein the bulbous tip portion is substantially semi-spherical.

5. The system of modular augments of claim 1, wherein the rotation element includes a cam lock.

6. The system of modular augments of claim 1, wherein the rotation element includes a gear.

7. The system of modular augments of claim 1, wherein the rotation element includes a worm gear.

8. The system of modular augments of claim 1, wherein the rotation element includes a captured nut.

9. The system of modular augments of claim 1, wherein the rotation element further comprises a rotatable nut or gear that when rotated translates the bulbous tip portion relative to the rotatable nut or gear.

10. The system of modular augments of claim 1, wherein the first augment second coupling element and the second augment first coupling element are shaped to interlock with one another.

11. The system of modular augments of claim 1, wherein the second augment second end portion has a second coupling element adapted to attach to a distally-located third augment.

12. The system of modular augments of claim 1, wherein when the first and second augments are coupled together and secured to the acetabular shell, the first and second augments form a single augment that extends in a direction away from the acetabular shell.

13. The system of modular augments of claim 1, wherein the first coupling element of the first augment first end portion is adapted to be coupled to a proximally-located third augment or an acetabular shell.

14. The system of modular augments of claim 1, wherein the first augment first coupling element is adapted to attach to a third augment, the third augment extending from a first end portion having a first coupling element to a second end portion having a second coupling element, wherein the third augment second coupling element has a complementary geometry to mate with the first augment first coupling element.

15. A system for supporting an acetabular shell at a bone, the system comprising:
an acetabular shell having a first surface, a second surface; and an opening extending from the first surface to the second surface;
an augment including a body having a first surface arranged to face the bone and a second surface opposite the first surface arranged to face away from the bone, the body extending from a first end portion to a second end portion, the first end portion positionable adjacent to the acetabular shell and having a first coupling element, and the second end portion having a second coupling element, the first coupling element having an extension portion and a bulbous tip portion, wherein the extension portion is adapted to extend through the opening of the acetabular shell from the first surface to the second surface, and the bulbous tip portion is adapted to be captured in the acetabular shell, and
wherein the first coupling element includes a rotation element that when rotated, translates the extension portion and the bulbous tip portion relative to the rotation element.

16. The modular augment of claim 15, wherein the first end portion has a curved surface that is shaped to conform to a generally spherical surface portion of the acetabular shell.

17. The modular augment of claim 15, wherein the first surface comprises a porous material that promotes boney ingrowth adapted to face the bone when implanted, and wherein the second surface comprises a smooth surface adapted to face away from the bone when implanted.

18. An augment and acetabular shell system comprising:
an acetabular shell having a first surface and a second surface, and an opening extending from the first surface to the second surface;
an augment having a first coupling element; and
an elongate coupling member having an extension portion and a bulbous tip portion, wherein the extension portion is adapted to extend through the opening from the first surface to the second surface, and the bulbous tip portion is adapted to be captured in the acetabular shell,
wherein the first coupling element includes a rotation element that when rotated, translates the elongate coupling member relative to the rotation element.

19. The system of claim 18, wherein the bulbous tip portion is three-dimensionally rotatable within the opening to adjust an orientation of the augment with respect to the shell.

20. The system of claim 18, wherein the rotation element includes a captured nut.

* * * * *

UNITED STATES PATENT AND TRADEMARK OFFICE
CERTIFICATE OF CORRECTION

PATENT NO. : 10,751,186 B2  
APPLICATION NO. : 16/040894  
DATED : August 25, 2020  
INVENTOR(S) : Jacob Macke Page 1 of 1

It is certified that error appears in the above-identified patent and that said Letters Patent is hereby corrected as shown below:

In the Claims

In Column 18, Line 6, in Claim 15, delete "surface;" and insert --surface,-- therefor Signed and Sealed this  
Twenty-fourth Day of November, 2020

Andrei Iancu  
*Director of the United States Patent and Trademark Office*